United States Patent [19]

Tanimoto et al.

[11] Patent Number: 5,447,732
[45] Date of Patent: Sep. 5, 1995

[54] HIGH-ABSORPTION MINERAL-CONTAINING COMPOSITION AND FOODS

[75] Inventors: Hiroyuki Tanimoto; Hitoshi Sato; Chiya Kuraishi; Keishi Kido; Katsuya Seguro, all of Kawasaki, Japan

[73] Assignee: Ajinomoto Co., Inc., Tokyo, Japan

[21] Appl. No.: 319,483

[22] Filed: Oct. 7, 1994

Related U.S. Application Data

[63] Continuation of Ser. No. 125,829, Sep. 24, 1993, abandoned.

[30] Foreign Application Priority Data

Nov. 25, 1992 [JP] Japan .................. 4-315367

[51] Int. Cl.$^6$ .................................. A23L 1/305
[52] U.S. Cl. .......................... 426/74; 426/656
[58] Field of Search .................. 426/74, 656

[56] References Cited

U.S. PATENT DOCUMENTS 5,292,538  3/1994  Paul et al. ................... 426/74
5,296,246  3/1994  Inoue et al. .................. 426/74

FOREIGN PATENT DOCUMENTS 0284386  9/1988  European Pat. Off. .

OTHER PUBLICATIONS

Patent Abstracts of Japan, vol. 15, No. 150 (C-0824), Apr. 16, 1991, JP-A-3030648, Feb. 8, 1991.
Patent Abstracts of Japan, vol. 15, No. 189 (C-0831), May 15, 1991, JP-A-3047087, Feb. 28, 1991.
Patent Abstracts of Japan, vol. 17, No. 429 (C-1095), Aug. 10, 1993, JP-A-5095767, Apr. 20, 1993.

*Primary Examiner*—Helen Pratt
*Attorney, Agent, or Firm*—Oblon, Spivak, McClelland, Maier & Neustadt

[57] ABSTRACT

To provide a composition containing a mineral absorption accelerator which accelerates the absorption of minerals. It contains minerals and degraded products of poly-γ-glutamic acid as a mineral absorption accelerator and may be used in foods in a variety of forms, including a beverage, gel, solid or powder form.

15 Claims, 3 Drawing Sheets

HIGH-ABSORPTION MINERAL-CONTAINING COMPOSITION AND FOODS

This application is a continuation of application Ser. No. 08/125,829, filed on Sep. 24, 1993, now abandoned.

BACKGROUND OF THE INVENTION

1. Field of the Invention

The present invention relates to a composition which has an accelerated mineral-absorbing effect and foods containing it. More specifically, it relates to a composition which contains minerals and poly-γ-glutamic acid degraded product as a mineral-absorbance accelerating additive, and foods containing them.

2. Discussion of the Background

The human body comprises about 20 minerals, and of these Japanese people tend to be deficient in calcium, iron, zinc, copper, magnesium and other minerals, creating what is considered to be a dietary problem. In particular, the deficiencies are in calcium and iron.

In the case of calcium, the recommended daily allowances for adults has been set at 600 mg, and while the national average intake per capita is slightly lower at 540 mg (1989 national nutrition survey), a reduced intestinal absorption rate of calcium due to a variety of causes has led to the problem of calcium deficiency in the body. Osteoporosis, which occurs with high frequency among the elderly, is mainly related to a breakdown in the balance between calcium intake and excretion, and this becomes a major cause for the increase in bed-ridden elderly. Osteoporosis occurs with particularly high frequency among postmenopausal women, and one of the causes of this is thought to be the considerable lowering in secretion of female hormone (estrogen) and the lowering of the calcium absorption rate by the small intestine. The number of osteoporosis patients is increasing year by year, and is presently reported to be about 5 million.

In the case of iron, the recommended daily allowances for adults has been set at 11 mg (10 mg for men, 12 mg for women), and the national average intake per-capita is 11.4 mg (1989 national nutrition survey), barely fulfilling the recommended daily allowances as an average for men and women, while the problem of iron deficiency occurs particularly among menstruating women. It has been calculated that menstruating women excrete about twice the amount of iron per day as adult males, and thus the balance of iron in the body tends towards a lack thereof. The results of surveys reveal that 40–60% of menstruating women suffer from iron deficiency anemia.

Generally, it is considered that minerals must be present in the small intestine in a soluble state in order to be absorbed.

In the case of calcium, there are two routes for absorption, active transport controlled by the regulation of vitamin D and various hormones whereby calcium is absorbed in the upper small intestine against a concentration gradient, and passive transport whereby calcium in the lower small intestine is absorbed following a concentration gradient. However, when calcium is present in large amounts in the intestine, such as during the intake of food, the proportion of the passive transport from the lower small intestine is overwhelmingly high, and in contrast to the case of the active transport which cannot rise above a certain amount even if the concentration of calcium increases, the passive transport rises as the amount of the soluble calcium concentration in the intestine increases (Am. J. Physiol., 240, 32, 1981). In general, the rate of absorption of calcium in the intestines is reported to be 10–50%.

Iron is mainly absorbed in the upper small intestine, through the two modes of absorption of heme iron and nonheme iron. Whereas heme iron is absorbed as an iron porphyrin complex, nonheme iron is solubilized and liberated as a free ion before being absorbed (Gastroent., 58, 647, 1971). The absorption rate of iron is extremely low, being not greater than 10–20% for heme iron and 1%–5% for nonheme iron.

Casein phosphopeptide (CPP), a product of the enzymatic degradation of the milk protein casein, is an example of a substance which exhibits an accelerating effect on the absorption of calcium and iron by raising the concentrations of soluble calcium and soluble iron in the small intestine (Japanese Patent Publication No. HEI 02-7616, Japanese Patent Unexamined Publication No. SHO 59-162843). Calcium and iron are maintained in a soluble state by the chelating effect of the phosphate groups of phosphoserine and carboxyl groups of the acidic amino acids contained in CPP, which is therefore reported to produce an absorption accelerating effect thereon by increasing the concentrations of soluble calcium and soluble iron in the small intestine. However, the industrial production of CPP requires complicated procedures such as enzyme treatment, etc., and when added to food, its degradation proceeds even further during the course of its movement through the small intestine, sometimes leading to a loss in its ability to solubilize minerals.

Even if casein is consumed directly, it is degraded enzymatically in the intestine, producing CPP, and therefore mineral absorption is accelerated. However, in this case as well, the degradation is promoted in the intestine sometimes leading to a loss in its ability to solubilize minerals, while casein has disadvantages from the point of view of food processing, such as poor solubility (particularly in the acidic range), etc.

Furthermore, foods are sometimes mineral-enriched using inorganic mineral salts or mineral powders, but these have the possibility of producing insoluble salts with other copresent substances, and since the excessive intake of one type of mineral inhibits the absorption of other minerals, there is not much improvement in the utilization of minerals in the body. For example, a large intake of calcium inhibits the absorption of iron. Excessive mineral-enrichment of foods is disadvantageous in that the taste of foods is spoiled by harsh, astringent, pungent taste produced by the minerals.

Poly-γ-glutamic acid, present in the viscous substance of natto or secreted extracellularly by *Bacillus* bacteria such as *Bacillus natto* and the like, and synthetic poly-α-glutamic acid, both possess a solubilizing effect on minerals in the lower small intestine and accelerate mineral absorption (Japanese Patent Unexamined Publication No. HEI 03-30648). However, when used as a material for food, since poly-α-glutamic acid is synthetic, there is a problem of safety, the production process is laborious, and like CPP it is sometimes degraded by proteases during movement through the intestine. Poly-γ-glutamic acid present in the viscous substance of natto or poly-γ-glutamic acid secreted by *Bacillus natto* bacteria such as *Bacillus natto* under normal culturing conditions both have a high viscosity, and therefore the labor required during their preparation and food processing treatment has been a disadvantage.

SUMMARY OF THE INVENTION

The object of the present invention is to develop an ingredient whose preparation is relatively simple, which has a favorable solubility for application in food processing, which may be used in a wide range of foods, and which maintains its activity in the small intestine, and to develop thereby a composition which has an accelerating effect on mineral absorption while masking the extraneous taste of enriched minerals.

Another object of the present invention is to provide a method for accelerating the absorption of a mineral in a mammal.

Another object of the present invention is to provide a method for administering a mineral to a mammal.

The objects of the present invention is provided for based on the discovery that poly-α-glutamic acid can be degraded by proteases due to the α-bond whereas poly-γ-glutamic acid cannot be degraded by proteases due to the γ-bond, that lowering the molecular weight of poly-γ-glutamic acid present in the viscous substance of natto or secreted by *Bacillus natto* or the like under normal culturing conditions leads to its lower viscosity and facilitates its preparation and food processing treatment, and therefor that poly-γ-glutamic acid degraded products of molecular weight $1 \times 10^4$- $3 \times 10^5$ solubilize minerals in the small intestine and does not lose this solubilizing activity on minerals in the small intestine even when added to foods. Furthermore, we have discovered that poly-γ-glutamic acid imparts a mellow taste to foods, while masking the harsh, astringent, pungent taste produced by enriched minerals, and as a result of developmental research we have succeeded in developing a composition by which minerals may be easily supplemented to the body, thus completing the present invention.

In other words, the present invention relates to a composition which contains minerals and poly-γ-glutamic acid degraded products as a mineral absorption accelerator, and to foods which contain them and thus have an accelerating effect on the absorption of minerals.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DETAILED DESCRIPTION OF THE PREFERRED EMBODIMENTS

Figure 1:
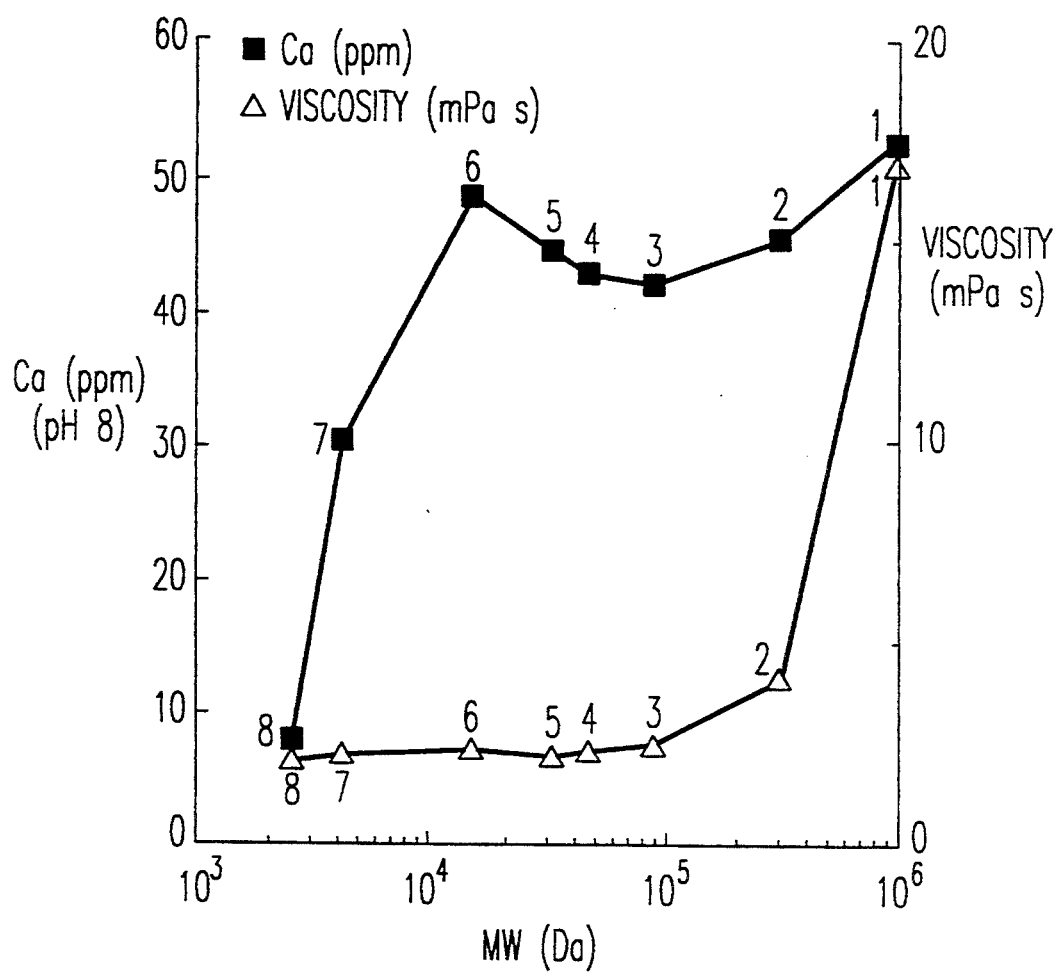
FIG. 1 shows the relationship between the molecular weight (Mw) of poly-γ-glutamic acid, calcium concentration, and the viscosity of poly-γ-glutamic acid solutions.

The minerals to be used according to the present invention include any or all of the life-essential minerals, including calcium, iron, magnesium, zinc, copper, etc. Also, there is no restriction on the form of the mineral to be used, but chemically synthesized food additives such as calcium chloride, calcium citrate, calcium glycerophosphate, calcium gluconate, calcium hydroxide, calcium carbonate, calcium lactate, calcium pantothenate, dihydrogen calcium pyrophosphate, calcium sulfate, calcium triphosphate, calcium monohydrogen phosphate, calcium dihydrogen phosphate, etc. and natural calcium sources such as shell calcium and bone calcium are preferred.

As for iron, chemically synthesized food additives such as ferric chloride, sodium ferrous citrate, iron citrate, ammonium iron citrate, ferrous gluconate, iron lactate, ferrous pyrophosphate, ferric pyrophosphate, ferrous sulfate and natural iron sources such as heme iron are preferred.

The poly-γ-glutamic acid to be used according to the present invention may be poly-γ-glutamic acid extracted from the viscous substance of natto, or it may be poly-γ-glutamic acid secreted extracellularly of bacteria belonging to the genus *Bacillus*, such as *Bacillus natto*, *Bacillus licheniformis*, *Bacillus subtills*, and *Bacillus subtilis var. polyglutamicum* etc. Also, there is absolutely no problem with including the levan contained in the viscous substance of natto or secreted simultaneously by *Bacillus natto*. As bacteria are *Bacillus natto* ATCC 15245, *Bacillus licheniformis* ATCC 9945A, *Bacillus subtills* NRRL B-2612, and *Bacillus subtilis var. polyglutamicum* etc. Natto, as described above, is a traditional fermentation food in Japan made of soy beans. There are also such kinds of soy bean fermentation foods in other Asian countries, however, Natto is a wet and sticky food while the other foods in the other Asian countries are the dry type. The ingredients which give the sticky characteristics to Natto are poly-γ-glutamic acid and levan.

For the production of poly-γ-glutamic acid with the desired molecular weight, there is a method whereby the molecular weight of poly-γ-glutamic acid with a molecular weight higher than that desired is lowered by an acid or by special enzymes not present in the intestines, which degrades γ-bonds, and a method whereby poly-γ-glutamic acid of the desired molecular weight ($1 \times 10^4$- $3 \times 10^5$ as determined by the low angle laser scattering meter method) is secreted by culturing *Bacillus natto*, etc.; however, there is no difference with using either source of poly-γ-glutamic acid.

Sources of suitable enzymes include the product of autolysis of bacteria sources which produce poly-γ-glutamic acid, *Bacillus natto* phage, *Flavobacterium polyglutamicum*, *Aspergilus oryzae* and enzyme extracts of animal tissue such a blood, brain, liver, spleen and kidney.

The poly-γ-glutamic acid preferably has a viscosity of from 4.2–2.2 mPas, more preferably 2.54–2.44 mPas, when measured as a 2 mg/ml, 20 mM Tris-HCl buffer, pH 7.2 solution using a digital rotational viscometer manufactured by Toyo Seiki, Inc.

Poly-γ-glutamic acid is usually obtained as a sodium salt, but there is no difference with using its other salts or the free polyglutamic acid.

If the composition is used as a food, such as a seasoning suitable examples may be a Japanese-style seasoning such as soup stock or noodle broth, table vinegar, sweet sake, miso, Worcester sauce, Chinese-style seasoning mixtures, retort liquid seasonings, Western-style soup stock, pasta sauce, curry roux, retort curry, seasonings for seasoned non-coated frying and fried chicken, or fish flour for cooked rice and base for boiled rice with tea, etc.

If the composition is used as a food, such as a processed meat or fish suitable examples include, hamburger, meat balls, sausage, ham, boiled fish paste, chikuwa fish paste, fish balls, fish sausages, as well as corned beef, beef cooked Japanese-style and boiled fish, oil-packed and other canned foods, and there is no problem with using either refrigerated foods or frozen foods.

If the composition is used as a food, such as a processed oil or fat, suitable substances, may be any number of processed oils or fats which do not contain whole eggs, cryopreserved eggs, egg yolk or powdered egg white, and may include, for example, dressing, butter cream, animal or vegetable cream, shortening, margarine, chocolate, etc.

If the composition is used as a food, such as dairy product suitable examples may be, cheese, processed cheese products, yogurt, white sauce and foods containing white sauce such as cream croquette, gratin, etc.

If the composition is used as a food, such as a beverage or soup which does not contain polyphenol suitable examples are one which does not contain polyphenol derived from fruit juice, coffee, tea, grape wine, etc. For example, the beverage may be refreshment beverages such as dairy beverages, lactic bacterium beverages, soybean milk, sports drinks, nutritional drinks, cider, etc. The soup may be a homogeneous pottage, consomme soup or Chinese-style soup which does not contain soy grains or cereal grains, and the high-absorption mineral-containing composition is contained in their liquid portion.

If the composition is used as a food, such as a confectionery suitable examples are not a so-called bakery product such as cookies or pie, but may be, for example, candy or caramel, as well as candy drops, sweet bean jelly, jellies which use gelatin or pectin, desserts which use agar, etc.

If the composition is used as a food, such as a cereal suitable examples may be, corn flakes, brown rice flakes, etc.

If the composition is used as a food, such as a flour-based food, flour-based food which is not a so-called bakery product or noodles, and may be, for example, premixed flour such as vegetable pancake mix or steam pan mix, rice cakes, crumbs, fen-tiao (sticks of bean jelly), hi-fun (rice flour-based noodles), shira-tama-ko (a bleaching powder made from glutinous rice), jo-shinko (a confectionery stockmade from nonglutinous rice), or Japanese confectioneries which use them.

An explanation will now be provided regarding the amounts of poly-γ-glutamic acid to be added according to the present invention. There is no limit on the proportion of poly-γ-glutamic acid to be added, but generally it may be added at about 0.1–10 wt % for dried foods and 0.01–5 wt % for beverages based on the total weight of the food.

Minerals such as calcium and iron are simultaneously added for enrichment, and calcium is added to provide from 30 mg–300 mg, and preferably 100 mg–200 mg of available calcium per serving for beverages, and 50 mg–3000 mg, and preferably 100 mg–1000 mg of available calcium per serving for gels, solids and flour granules, while iron is added at 0.5 mg–100 mg, and preferably 1 mg–40 mg of available iron per serving for beverages, and 1 mg–1000 mg, and preferably 2 mg–500 mg of available iron per serving for gels, solids and flour granules.

When the composition is added to food products, it imparts a mellow taste thereto and is able to mask the harsh, astringent, pungent taste caused by reinforcement of minerals, and therefore even if the minerals are reinforced in the foods to the above amounts, there is no effect at all on the taste of the foods.

The present invention also provides for a method of accelerating the absorption of a mineral in a mammal, preferably a human, by administering poly-γ-glutamic acid degraded products and said mineral. Administration may be oral or intravenous. In the case of oral administration, this can be achieved by administering a mineral-enriched composition such as one of the food compositions herein described. Such food compositions generally contain from 0.1–10 wt % poly-γ-glutamic acid for dried foods and from 0.01–5 wt % for beverages. The molecular weight of said poly-γ-glutamic acid is generally in the range of from $1\times 10^4$ -$3\times 10^5$.

The present invention also provides for a method of administering a mineral to a mammal, preferably a human, by administering poly-γ-glutamic acid degraded products and said mineral. Administration may be oral or intravenous. In the case of oral administration, this can be achieved by administering a mineral-enriched composition such as one of the food compositions herein described. Such food compositions generally contain from 0.1–10 wt % poly-γ-glutamic acid for dried foods and from 0.01–5 wt % for beverages. The molecular weight of said poly-γ-glutamic acid is generally in the range of from $1\times 10^4$-$3\times 10^5$.

Having generally described this invention, a further understanding can be obtained by reference to certain specific examples which are provided herein for purposes of illustration only and are not intended to be limiting unless otherwise specified.

EXAMPLE 1

Preparation of poly-γ-glutamic acid

To 500 g of commercially available wet natto (a traditional fermentation food in Japan made of soy beans) was added 1,500 ml of distilled water, and after thorough washing and dissolution of the viscous substance, the bean portion was removed using a filtering cloth. The viscous filtrate was subjected to centrifugation separation, and the supernatant thereof was adjusted to pH 2.0 using hydrochloric acid. After removal of the precipitate by centrifugal separation, 150 g of sodium chloride was added thereto to precipitate the poly-γ-glutamic acid. After collection of the precipitate by centrifugal separation, it was dissolved and neutralized in a sodium hydroxide solution. It was then dialyzed against water and lyophilized, to obtain 2 g of poly-γ-glutamic acid as a sodium salt. The molecular weight of the prepared poly-γ-glutamic acid was measured with a low angle laser scattering meter (LALLS: Tosoh LS8000) and found to be $9.27\times 10^5$.

EXAMPLE 2

Degradeability of poly-α or -γ-glutamic acid by proteases

The results of investigation of the degradeability by proteases of synthesized poly-α-glutamic acid (molecular weight 80,000) and the poly-γ-glutamic acid prepared in Example 1 above are shown in Table 1. The enzymes were added at 10 U per 1 mg of polyglutamic acid, and the reaction was conducted at 37° C. for 24 hours. Movement of the peak for polyglutamic acid in gel filtration HPLC to the low molecular end or disappearance altogether upon action of the enzyme led to the judgment that it had been degraded.

of 60 rpm (rotor: HM-1). The results are shown in Table 4 and FIG. 1.

TABLE 4

|  | Sample 1 | Sample 2 | Sample 3 | Sample 4 | Sample 5 | Sample 6 | Sample 7 | Sample 8 |
|---|---|---|---|---|---|---|---|---|
| Viscosity (mPas) | 16.9 | 4.20 | 2.54 | 2.43 | 2.24 | 2.44 | 2.35 | 2.20 |

TABLE 1

| Enzyme | Trypsin | Chymotrypsin | Pepsin | Elastase | Thermolysin | Pronase | Y8 Protease | Aspergillus Protease |
|---|---|---|---|---|---|---|---|---|
| poly-α-glutamic acid | x | x | x | x | x | O | O | O |
| poly-γ-glutamic acid | x | x | x | x | x | x | x | x |

(O: degraded; x: not degraded)

EXAMPLE 3

Lowering of molecular weight of poly-γ-glutamic acid

The poly-γ-glutamic acid prepared in Example 1 was dissolved to a concentration of 2 mg/ml, and the solutions were adjusted to pH 1 with hydrochloric acid, and then heated at 50° C. or 70° C. for 30 minutes to 6 hours. After heating, the solutions were returned to room temperature and then neutralized with a sodium hydroxide solution, dialyzed against water and lyophilized. The molecular weights of the resulting poly-γ-glutamic acid degradated products were measured by LALLS, and the results are shown in Table 2.

TABLE 2

|  | Sample 1 | Sample 2 | Sample 3 | Sample 4 | Sample 5 | Sample 6 | Sample 7 | Sample 8 |
|---|---|---|---|---|---|---|---|---|
| Temperature (°C.) | — | 50 | 50 | 50 | 50 | 70 | 70 | 70 |
| Time (hr) | — | 0.5 | 2 | 4 | 6 | 1 | 3 | 5 |
| Molecular weight (Da) × $10^4$ | 92.7 | 30.3 | 8.80 | 4.78 | 3.30 | 1.50 | 0.420 | 0.256 |

EXAMPLE 4

Calcium solubilization test

For each poly-γ-glutamic acid solution prepared in Example 3 (1 mg/ml), 0.5 ml was premixed with 0.5 ml of 10 mM calcium chloride solution, and then 1.0 ml of 20 mM phosphate buffer solution of pH 7 or 8 was added thereto, and the solutions were incubated at 37° C. for 2 hours and then subjected to centrifugal separation. The resulting calcium phosphate precipitate was removed, the concentration of calcium in the supernatant was measured by the atomic absorption method, and the rate of residue was determined with the remaining calcium as soluble calcium. As a comparison, the same test was conducted using distilled water. The results are shown in Table 3 and FIG. 1 (results at pH 8)

EXAMPLE 6

Masking of extraneous taste of calcium

The masking effect of the astringent, pungent taste of calcium, upon the addition of the poly-γ-glutamic acid degradated product prepared in Example 3, Sample 2 to calcium chloride solutions (0.5%, 1.0%, 2.0%) to amounts of 0.25% and 0.5% were determined by a panel of 4 people. In the evaluation, an astringent pungent taste which was strongly noticeable was assigned 4 points, noticeable was assigned 3 points, slightly noticeable was assigned 2 points, and unnoticeable was assigned 1 point. The averages of the results from the 4 people are shown in Table 5.

TABLE 5

|  | CaCl₂ solution (%) | | |
|---|---|---|---|
| Poly-γ-glutamic acid (%) | 2.0 | 1.0 | 0.5 |
| 0 | 4.0 | 4.0 | 3.5 |
| 0.25 | 3.75 | 3.0 | 2.25 |
| 0.5 | 3.25 | 2.25 | 1.75 |

EXAMPLE 7

Masking of extraneous taste of iron

The masking effect of the astringent, extraneous taste (the characteristic blood-like taste of iron) of iron upon the addition of the poly-γ-glutamic acid degradated product prepared in Example 3, Sample 2 to ferrous sulfate solutions (0.1%, 0.5%, 1.0%) to amounts of 0.25% and 0.5% were determined by a panel of 4 people. In the evaluation, an astringent, extraneous taste

TABLE 3

| | Rate of residue of soluble calcium (%) | | | | | | | | |
|---|---|---|---|---|---|---|---|---|---|
|  | Sample 1 | Sample 2 | Sample 3 | Sample 4 | Sample 5 | Sample 6 | Sample 7 | Sample 8 | Distilled water |
| pH 7.0 | 32.6 | 27.8 | 26.8 | 27.1 | 27.2 | 32.6 | 20.4 | 13.5 | 7.3 |
| pH 8.0 | 52.6 | 45.3 | 42.2 | 42.8 | 44.4 | 48.6 | 30.3 | 7.9 | 1.1 |

EXAMPLE 5

Measurement of viscosity

The viscosities of each poly-γ-glutamic acid solution prepared in Example 3 (2 mg/ml, 20 mM Tris-HCl buffer, pH 7.2) were measured using a digital rotational viscometer manufactured by Toyo Seiki, Inc. This was effected at a temperature of 23° C. and a rotation speed which was strongly noticeable was assigned 4 points, noticeable was assigned 3 points, slightly noticeable was assigned 2 points, and unnoticeable was assigned 1 point. The averages of the results from the 4 people are shown in Table 6.

TABLE 6

| Poly-γ-glutamic acid (%) | FeSO₂ solution (%) | | |
|---|---|---|---|
| | 1.0 | 0.5 | 0.1 |
| 0 | 4.0 | 4.0 | 2.5 |
| 0.25 | 3.0 | 2.75 | 1.5 |
| 0.5 | 2.5 | 1.75 | 0.75 |

It is clear from the above experiments that poly-γ-glutamic acids with molecular weights of $1 \times 10^4$-$3 \times 10^5$ possess the ability to solubilize calcium, while having a low viscosity and protease resistance, and that it masks the extraneous taste of calcium and iron. That it possesses the ability to solubilize calcium in the small intestine as well is clear from Japanese Patent Unexamined Publication HEI 03-3648, and thus it is shown that poly-γ-glutamic acids of molecular weights $1 \times 10^4$-$3 \times 10^5$ accelerate the absorption of calcium in the small intestine.

Regarding minerals other than calcium, poly-γ-glutamic acid has as expected the same accelerating effect on solubilization thereof in the small intestine, and therefore accelerates their absorption in the small intestine.

EXAMPLE 8

Iron absorption test

Figure 2:
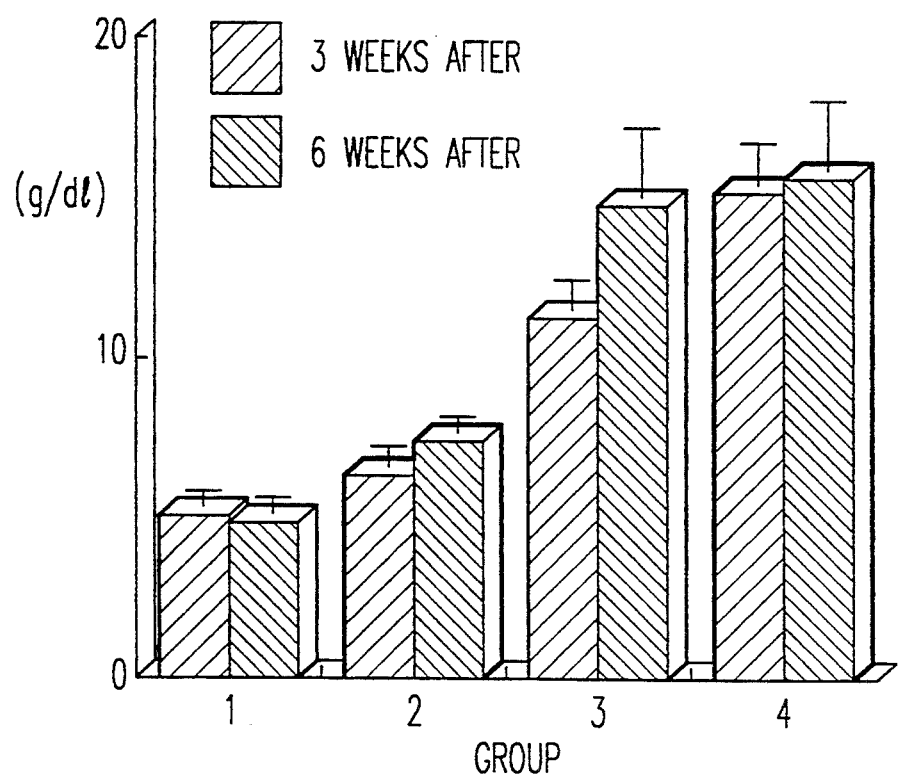
FIG. 2 shows the results of measurement of the hemoglobin value in Example 8.
Figure 3:
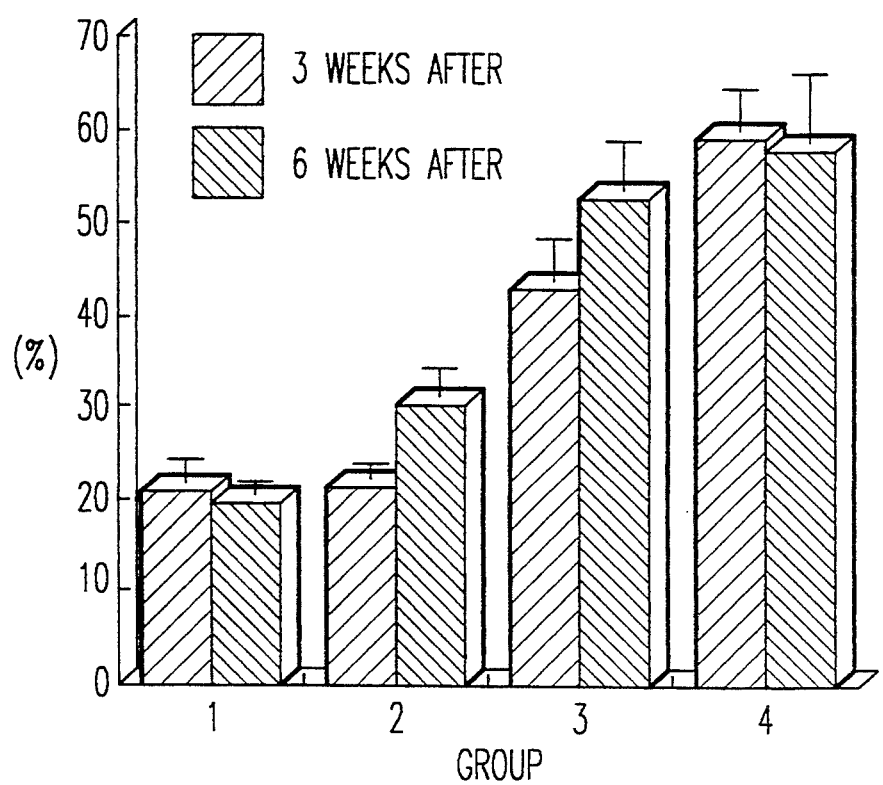
FIG. 3 shows the results of measurement of the hematocrit value in Example 8.

Just-weaned male Wistar rats (body weight about 50 g) were pre-raised for 3 weeks on iron-deficient feed (20% casein diet, iron content 3 ppm). At the end of the 3 weeks, blood was taken from the caudal vein, and those rats with a hemoglobin value of 7 g/dl or lower were used as anemic rats, and provided for the following experiment. The anemic rats were divided into 4 groups (8 rats per group), further given the above mentioned iron-deficient feed, and further raised for 6 weeks (only one group was given a standard feed (iron content 150 ppm) Also, preparations containing 1 ml of the feeds listed in Table 7 dissolved in distilled water were given orally each morning. The improving effect on the anemia was judged by taking blood from the caudal vein once a week and measuring the hemoglobin value and hematocrit value. The results are shown in Table 8 and FIGS. 2 and 3.

TABLE 7

| Group | Feed | Sample | Dosage | Iron dosage |
|---|---|---|---|---|
| 1 | Iron-deficient feed | H₂O | 1 ml/day | 0 μg |
| 2 | Iron-deficient feed | FeSO₄ | 250 μg/ml/day | 50 μg |
| 3 | Iron-deficient feed | FeSO₄ —PGA | 250 μg(FeSO₄) +35 μg(PGA)/ml/day | 50 μg |
| 4 | Standard feed | H₂O | 1 ml/day | 0 μg |

PGA = poly γ-glutamic acid according to Example 3, Sample 2

TABLE 8

| Group | After 3 weeks | | After 6 weeks | |
|---|---|---|---|---|
| | Hemoglobin value (g/dl) | Hematocrit value (%) | Hemoglobin value (g/dl) | Hematocrit value (%) |
| 1 | 5.1 ± 0.5[2] | 20.4 ± 3.0[2] | 4.9 ± 0.5[1,2] | 19.1 ± 1.8[1,2] |
| 2 | 6.3 ± 0.7[2] | 20.9 ± 1.9[2] | 7.3 ± 0.6[2] | 30.0 ± 3.2[2] |
| 3 | 11.2 ± 0.9[1] | 42.8 ± 4.3[1] | 14.6 ± 2.2[1] | 52.3 ± 5.4[1] |
| 4 | 14.9 ± 1.5[1,2] | 58.5 ± 6.1[1,2] | 15.4 ± 2.3[1] | 57.3 ± 4.5[1] |

(Average ± SD)

[1]Significant difference for Group 2
[2]Significant difference for Group 3

The above results prove that, since the polyglutamic acid accelerates the absorption of iron, the improving effect on the anemic Group 3 provided a restoration to the same levels as Group 4 which was given the standard feed.

EXAMPLE 9

Accelerating effect on calcium absorption

Five-week-old male Wistar rats (body weight about 130 g) were dissected at the abdomen under nembutal anesthesia, and 8 cm of the ileum (at 12 cm - 20 cm from the caecum) were ligated after washing and removing the contents of the intestine. A solution containing 10 mM of CaCl₂, 10 μCi of ⁴⁵CaCl₂, 20 mM of a phosphate buffer (pH 8.0) and 2 mg/ml of each sample was injected into the ligated intestine, after which the intestine was returned into the abdominal cavity, and the rats were allowed to remain at a controlled temperature of 37° C. Portal blood was taken at 5, 15, 30 and 60 minutes after the injection, and the fumer was taken at 30 and 60 minutes thereafter, and the respective amounts of ⁴⁵Ca were determined with a liquid scintillation counter.

| | |
|---|---|
| Control Example 1 | Distilled water |
| Control Example 2 | CPP (CPP-III, product of Meiji Seika, Inc.) |
| Test Example 1 | poly-γ-polyglutamic acid (molecular weight $3 \times 10^5$) |

Figure 4:
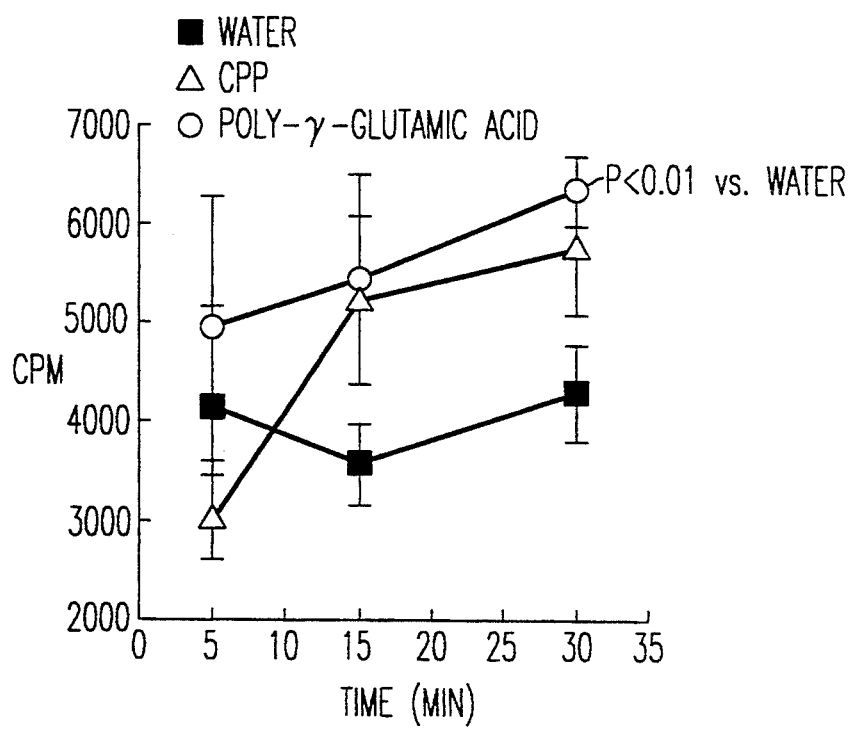
FIG. 4 shows the results of $^{45}$Ca amount in the portal blood in Example 9.
Figure 5:
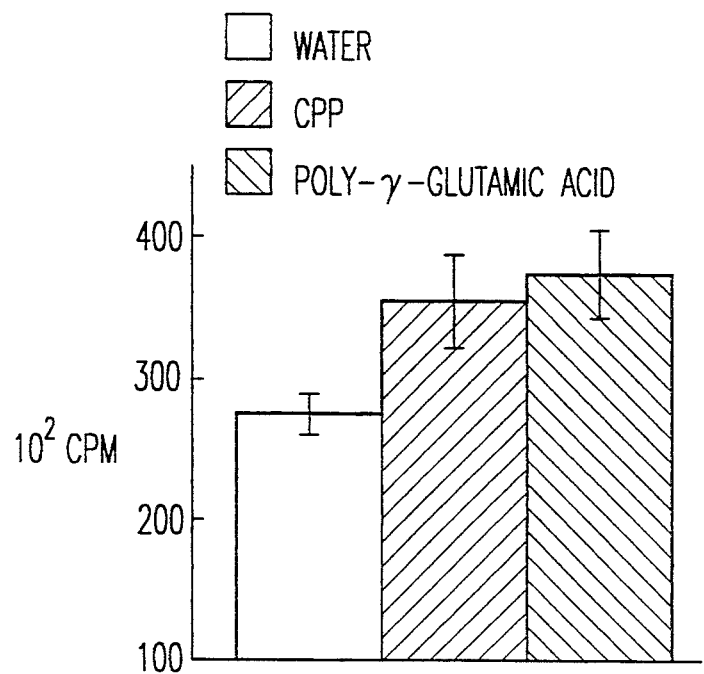
FIG. 5 shows the results of $^{45}$Ca amount in the fumer in Example 9.

The results from the portal blood are shown in FIG. 4, and the results from the fumer are shown in FIG. 5. It is confirmed from FIGS. 4 and 5 that poly-γ-polyglutamic acid has an accelerating effect on the absorption of calcium in the intestine even better than that observed for casein phosphopeptide (CPP).

EXAMPLE 10

Application in foods

Foods containing the poly-γ-glutamic acid degraded product prepared in Sample 2 of Example 3 and the results of the organoleptic tests conducted therefor will now be presented.

| [10-1 Curry] Composition of curry (8 person portion) | |
|---|---|
| Flour | 125 g |
| Butter | 100 g |
| Curry powder | 20 g |
| Sodium poly-γ-glutamate | 8 g |
| Calcium carbonate | 4 g |
| Beef | 400 g |
| Onion | 600 g |
| Butter (for frying) | q.s. |
| Potato | 300 g |
| Carrot | 150 g |
| Water | 1400 ml |
| Seasoning | q.s. |

Butter was melted in a frying pan and flour was placed therein to make brown roux, and then the curry powder, poly-γ-glutamic acid and calcium carbonate were added thereto and cooked slightly to make curry roux. The beef was cut into mouthsize pieces, fried in butter, and then water was added thereto for stewing. At this point, the previously prepared curry roux was slowly added thereto, and the mixture was stewed on low flame for 30 minutes. The curry prepared in this manner was apportioned into retort packs for retort sterilization. This curry contains approximately 200 mg of calcium per serving, and since poly-γ-glutamic acid is ingested therewith, the calcium of such curry is absorbed into the body in an efficient manner. Also, there was no difference in taste, feel or smell even when compared to control foods which did not contain poly-γ-glutamic acid and calcium carbonate.

| [10-2 Hamburger] Composition of hamburger | |
| --- | --- |
| Beef | 700 g |
| Pork | 300 g |
| Onion | 200 g |
| Whole egg | 150 g |
| Bread flour | 150 g |
| Seasoning | 20 g |
| Spice | 4 g |
| Sodium poly-γ-glutamate | 0.762 g |
| Calcium carbonate | 5 g |

Using the above composition, chopped beef and pork, minced and fried onion and the other materials were mixed well with a mixer, and then formed into 10 aliquot, and frozen at −18° C. to prepare raw frozen hamburger. The prepared hamburger contained 0.05% (by weight) of sodium poly-γ-glutamate, and each hamburger contained 200 mg of calcium. This corresponds to about ⅓ of the recommended daily allowances of calcium, and since it is consumed with poly-γ-glutamic acid which accelerates its absorption, it was assumed to be absorbed efficiently in the body. When the raw frozen hamburger was cooked, and compared to control foods which did not contain poly-γ-glutamic acid and calcium carbonate, the taste was pleasant with no difference in feel, taste and smell compared to the control foods.

| [10-3 Boiled fish paste] Composition of boiled fish paste | |
| --- | --- |
| Frozen ground fish | 1100 g |
| Soy protein | 160 g |
| Seasoning | 30 g |
| Sugar | 40 g |
| Sweet sake | 40 g |
| Potato starch | 100 g |
| Water | 660 g |
| Sodium poly-γ-glutamate | 10 g |
| Calcium carbonate | 20 g |

The ground fish and other ingredients were combined, ground with table salt, molded and heated to obtain boiled fish paste. The obtained fish paste was characterized by containing an abundant amount of easily absorbable calcium.

| [10-4 Cream croquette] Composition | |
| --- | --- |
| Flour | 100 g |
| Butter | 100 g |
| Water | 600 g |
| Milk | 900 g |
| Seasoning | 10 g |
| Minced meat | 100 g |

| [10-4 Cream croquette] Composition | |
| --- | --- |
| Sodium poly-γ-glutamate | 1.18 g |

To 100 g of butter was added 100 g of flour and the mixture was stirred and heated to make roux, after which the other materials were added thereto, and the mixture was heated and kneaded to make white sauce, which was then cooled to normal temperature. A coating was placed on this and portions were placed into heated oil and deep fried until the surface became light brown. Each croquette (about 30 g) contained approximately 15 mg of calcium due to the milk, and since poly-γ-glutamic acid was also contained therein, the ingested calcium was assumed to be efficiently absorbed into the body. These compared favorably to control foods which contained no poly-glutamic acid, with respect to feel, taste and smell. [10-5 Pottage soup]

One gram of sodium poly-γ-glutamate was added to smooth pottage soup (containing strained vegetables, potatoes, etc.) to 0.05%, 2% methyl cellulose was added thereto, as well as bone calcium (baked calcium) to produce a calcium content of 0.075%, and a spray-type granulator was used to make granulated pottage soup base. When this pottage soup base was dissolved in hot water to make pottage soup, one serving (120 ml) of soup contained 90 mg of calcium, since poly-γ-glutamic acid is ingested therewith, the calcium of such soup is absorbed into the body in an efficient manner. Also, there was no loss in smoothness, taste or smell when compared to control foods which did not contain poly-γ-glutamic acid or bone calcium. [10-6 Sweet bean jelly]

A 2.6 g portion of agar was soaked in water and allowed to absorb sufficient water, after which it was washed and dehydrated, torn into small bits and placed into a pot into which 72 ml of water was added, and then the mixture was heated and mixed, until the agar fully dissolved. Also, 180 g of sugar, 6 g of sodium poly-γ-glutamate and 10 g of ferrous sulfate were added thereto and the mixture was heated to boiling, and after straining with a sieve, the filtrate was again boiled, 110 g of raw bean jam was added thereto, and the mixture was kneaded. This was poured into a can or other mold while still warm and allowed to cool and solidify to prepare sweet bean jelly. This sweet bean jelly exhibited no extraneous taste of iron.

| [10-7 Candy] Composition of candy | |
| --- | --- |
| Granulated sugar | 4000 parts |
| Water | 1200 |
| Malt syrup | 1000 |
| Poly-γ-glutamic acid | 6.2 |
| Calcium gluconate | 77.4 |
| Flavoring | 10 |

The sugar and water were placed in a thick copper pot, and upon boiling the malt syrup was added thereto and the mixture was boiled to about 150° C. After the poly-γ-glutamic acid and calcium gluconate were added thereto and thoroughly mixed therewith, the pot was taken off the flame and the flavoring was added. This was molded and cooled to obtain hard candy. This candy contained calcium and poly-γ-glutamic acid and the consumed calcium was assumed to be efficiently absorbed into the body.

| [10-8 Jelly] Composition of milk jelly | |
| --- | --- |
| Powdered gelatin | 10 g |
| Sugar | 80 g |
| Milk | 400 cc |
| Sodium poly-γ-glutamate | 2.5 g |
| Vanilla essence | q.s. |

The powdered gelatin was poured onto 4 tablespoons of water and allowed to swell. The sugar and gelatin were added to the milk, the mixture was put on flame and dissolved with slight mixing, and just before boiling the flame was extinguished and the vanilla extract was added thereto. The mixture was poured into a mold and cooled to obtain milk jelly. This milk jelly contained abundant calcium due to the milk, and since it was ingested with poly-γ-glutamic acid, the calcium was assumed to be efficiently absorbed into the body.

| [10-9 Skewer dumplings] Composition of dumplings | |
| --- | --- |
| Jo-shin-ko | 400 g |
| Shira-tama-ko | 80 g |
| Lukewarm water | 300 ml |
| Sodium poly-γ-glutamate | 3.9 g |
| Calcium carbonate | 3.12 g |

Lukewarm water was added to the above composition, and the mixture was thoroughly kneaded. The resulting dumpling seeds were placed together in a steamer, and steamed on high flame for 20 minutes. After steaming they were taken out while still hot, placed in water to cool, and then massaged well with a damp cloth. This was formed into bite-sized portions and pierced with skewers, and then dipped in soup consisting of sugar and soy sauce or, strained bean jam to obtain skewer dumplings. These skewer dumplings contained poly-γ-glutamic acid, and therefore the ingested calcium was expected to be efficiently absorbed into the body. [10-10 Vegetable pancakes]

To 500 g of vegetable pancake premixed powder containing mostly flour were added 2.5 g of sodium poly-γ-glutamate and 5.0 g of bone calcium, and the materials were thoroughly mixed. Water, egg, vegetables and meat were added thereto, and dissolved, after which the mixture was fried on a heated and greased iron hotplate to obtain vegetable pancakes. These vegetable pancakes contained calcium and poly-γ-glutamic acid, and therefore the ingested calcium was assumed to be efficiently absorbed into the body.

The present invention provides for a composition containing minerals and a mineral absorption accelerator, as well as to foods which contain them, and upon ingestion thereof the concentration of soluble minerals in the intestine is increased, thus the absorption of minerals is accelerated, thus offering the effects of mineral enrichment for growing children, prevention of bone disease typified by osteoporosis in the elderly, and avoidance of mineral unbalances which occur even in healthy people due to a high-protein diet, high-phosphate diet, etc.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A mineral-enriched composition comprising
   i) 0.1 to 10 wt %, based on the total weight of the composition, of poly-γ-glutamic acid degraded products of molecular weight $1 \times 10^4$- $3 \times 10^5$; and
   ii) a mineral selected from the group consisting of calcium, iron, magnesium, zinc, copper and mixtures thereof; wherein said composition is not a bakery product or noodles.

2. The mineral-enriched composition of claim 1 comprising 0.01-5 wt % of poly-γ-glutamic acid degraded products, based on the total weight of the composition.

3. The mineral composition of claim 1, wherein said mineral is calcium selected from the group consisting of calcium chloride, calcium citrate, calcium glycerophosphate, calcium gluconate, calcium hydroxide, calcium carbonate, calcium lactate, calcium pantothenate, dihydrogen calcium pyrophosphate, calcium sulfate, calcium triphosphate, calcium monohydrogen phosphate, calcium dihydrogen phosphate, shell calcium, bone calcium and a mixture thereof.

4. The mineral composition of claim 1, wherein said mineral is iron selected from the group consisting of ferric chloride, sodium ferrous citrate, iron citrate, ammonium iron citrate, ferrous gluconate, iron lactate, ferrous pyrophosphate, ferric pyrophosphate, ferrous sulfate, heme iron and a mixture thereof.

5. A food comprising
   i) a mineral-enriched composition according to claim 1 or claim 2; and
   ii) an edible substance.

6. The food of claim 5, wherein said food is selected from the group consisting of a liquid, powder and solid seasoning.

7. The food of claim 5, wherein said food is processed meat or fish.

8. The food of claim 5, wherein said food is processed oil or fat.

9. The food of to claim 5, wherein said food is a dairy product.

10. The food of claim 5, wherein said food is a beverage or soup which does not contain polyphenol.

11. The food of claim 5, wherein said food is a confectionery but not a bakery product.

12. The food of claim 5, wherein the food is a cereal.

13. The food of claim 5, wherein said food is a flour based food, but not a bakery product or noodles.

14. A method of accelerating the absorption of a mineral selected from the group consisting of calcium, iron, magnesium, zinc, copper and mixtures thereof in a mammal comprising administering poly-γ-glutamic acid degraded products of molecular weight $1 \times 10^4$- $3 \times 10^5$ and said mineral to said mammal.

15. A method of administering a mineral selected from the group consisting of calcium, iron, magnesium, zinc, copper and mixtures thereof to a mammal comprising administering poly-γ-glutamic acid degraded products of molecular weight $1 \times 10^4$-$3 \times 10^5$ and said mineral to said mammal.

* * * * *